United States Patent
Ness et al.

(10) Patent No.: US 10,247,670 B2
(45) Date of Patent: *Apr. 2, 2019

(54) REFLECTIVE SURFACE TREATMENTS FOR OPTICAL SENSORS

(71) Applicant: Apple Inc., Cupertino, CA (US)

(72) Inventors: Trevor J. Ness, Santa Cruz, CA (US); Chin San Han, Mountain View, CA (US); David I. Nazzaro, Groveland, MA (US); Marcelo M. Lamego, Cupertino, CA (US); Naoto Matsuyuki, Kasugai (JP); Wolf Oetting, San Jose, CA (US)

(73) Assignee: Apple Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/114,003

(22) Filed: Aug. 27, 2018

(65) Prior Publication Data

US 2018/0364162 A1    Dec. 20, 2018

Related U.S. Application Data

(63) Continuation of application No. 14/740,196, filed on Jun. 15, 2015, now Pat. No. 10,078,052.

(60) Provisional application No. 62/043,294, filed on Aug. 28, 2014.

(51) Int. Cl.
| | | |
|---|---|---|
| *A61B 5/04* | (2006.01) | |
| *G01N 21/55* | (2014.01) | |
| *G01N 21/47* | (2006.01) | |
| *A61B 5/00* | (2006.01) | |
| *A61B 5/021* | (2006.01) | |
| *A61B 5/024* | (2006.01) | |
| *A61B 5/08* | (2006.01) | |
| *A61B 5/145* | (2006.01) | |

(52) U.S. Cl.
CPC ............... *G01N 21/55* (2013.01); *A61B 5/00* (2013.01); *A61B 5/0059* (2013.01); *G01N 21/4738* (2013.01); *A61B 5/0002* (2013.01); *A61B 5/021* (2013.01); *A61B 5/024* (2013.01); *A61B 5/0816* (2013.01); *A61B 5/14532* (2013.01); *A61B 5/14542* (2013.01); *A61B 5/681* (2013.01); *A61B 5/7203* (2013.01); *G01N 2201/0221* (2013.01); *G01N 2201/0625* (2013.01)

(58) Field of Classification Search
USPC ........................................................ 600/476
See application file for complete search history.

(56) References Cited

U.S. PATENT DOCUMENTS

| | | | |
|---|---|---|---|
| 6,115,621 A | 9/2000 | Chin | |
| 6,343,233 B1 | 1/2002 | Chin et al. | |
| 6,491,647 B1 * | 12/2002 | Bridger | A61B 5/021 |
| | | | 128/900 |
| 7,890,153 B2 | 2/2011 | Hoarau | |
| 8,005,624 B1 | 8/2011 | Starr | |

(Continued)

*Primary Examiner* — Nicole F Lavert
(74) *Attorney, Agent, or Firm* — Joseph F. Guihan

(57) ABSTRACT

An electronic device includes one or more light emitters for emitting light toward an object and one or more light detectors for collecting light exiting the object. A reflective coating, surface, or surface finish can be applied adjacent to the area to which light is emitted and/or through which light exits in order to increase the light collected by the light detector. The reflective coating can be oriented so as to reflect light back into the object.

20 Claims, 6 Drawing Sheets

(56) References Cited

U.S. PATENT DOCUMENTS

| | | | |
|---|---|---|---|
| 9,314,197 B2 | 4/2016 | Eisen et al. | |
| 2005/0230603 A1* | 10/2005 | Langland | G01V 8/14 250/221 |
| 2013/0006074 A1 | 1/2013 | Pologe | |

* cited by examiner

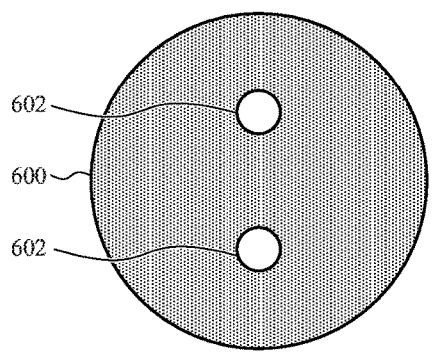
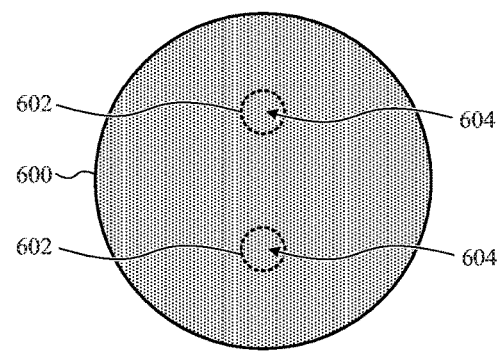
*FIG. 6A*  *FIG. 6B*

REFLECTIVE SURFACE TREATMENTS FOR OPTICAL SENSORS

CROSS-REFERENCE TO RELATED APPLICATION

This application is a continuation of U.S. patent application Ser. No. 14/740,196, filed Jun. 15, 2015, now U.S. Pat. No. 10,078,052, issued Sep. 18, 2018, which claims priority to U.S. provisional patent application No. 62/043,294, filed Aug. 28, 2014, both of which are hereby incorporated by reference herein in their entireties.

FIELD

This disclosure relates generally to sensor devices, and more particularly to electronic devices incorporating one or more optical sensing systems.

BACKGROUND

An electronic device can include an optical sensing system for quantifying surface or subsurface characteristics of an object onto which the electronic device is placed. The optical sensing system can include a light emitter to illuminate the object with light that may be absorbed or reflected by the object in a manner related to the characteristics of the surface or subsurface thereof. The optical sensing system may also include a light detector to generate electrical signals corresponding to light reflected from the object as a result of the illumination. These signals can be conveyed to the electronic device by the optical sensing system so that the electronic device can quantify characteristics of the surface or subsurface of the object.

In many cases, the electronic device may be undesirably responsive to noise (e.g., resulting from ambient light) present in the signals conveyed to it by an optical sensing system.

SUMMARY

Certain embodiments described herein reference an electronic device configured to quantify subsurface characteristics of an object onto which the electronic device is placed. In one aspect, an electronic device can be adapted to obtain physiological data from a biological subject after being placed in contact with or proximate to a surface of the subject. For example, an electronic device such as a wearable fitness device can be positioned against the skin of a user's wrist (hereinafter the "measurement site") and can obtain therefrom certain physiological data about the user such as heart rate, respiration rate, blood oxygenation, blood pressure, and so on.

In many embodiments, an electronic device (such as a smart watch, fitness device, cellular phone, tablet computer, other computing device, exercise equipment, exercise monitor, physiology monitor, and so on) can include an optical sensing system positioned behind or within one or more apertures defined within a bottom surface of the electronic device. The optical sensing system can include a light emitter (e.g., a light emitting diode) for illuminating a measurement site of an object and a light detector (e.g., a photodiode, a phototransistor, and/or an optical image sensor) for receiving light reflecting from the measurement site. In one aspect, the light emitter can be oriented to emit light toward a portion of the measurement site most adjacent to the light emitter (hereinafter the "illumination area"). Similarly, the light detector can be oriented to receive light exiting a portion of the measurement site most adjacent to the light detector (hereinafter the "collection area"). In many cases, the illumination area may be adjacent to the collection area. For example, in one embodiment, the illumination area and the collection area can be spaced one centimeter apart.

The electronic device can also include one or more reflectors positioned on or nearby the surface and adjacent to the one or more apertures defined therein. In some examples, the reflectors can be formed from mirrored films and can be positioned around the perimeter of the apertures.

Additional embodiments described herein may reference lenses positioned within each of the apertures defined by the bottom surface, disposed respectively over the light emitter and the light detector. One or more of the lenses may be formed from the same material as the surface, although this is not required. In one embodiment, one or more of the lenses can be configured to diffuse light. In other embodiments, one or more of the lenses can be configured to focus light onto a particular point or along a particular direction. In other embodiments, one or more of the lenses can be configured to polarize light to a particular orientation. In other embodiments, one or more of the lenses may be configured to exhibit transparency to a first frequency band of light and to exhibit opacity to a second frequency band of light. In one example, the first frequency band of light can be infrared light and the second frequency band of light can be green light. In some embodiments, a reflector as described above can be positioned around the perimeter of a bottom surface of a lens. In other embodiments, a lens can be formed from a multi-layered laminate material and a reflector can be interstitially disposed between the layers thereof. In some examples, each lens can be configured to provide the same functionality, although this is not required of all embodiments. For example, in some cases, different lenses can be configured to provide different functionality. For example, a lens positioned over a light emitter can be configured to focus light from the light emitter into the measurement site whereas a lens positioned over a light detector can be configured to focus light exiting the measurement site onto the light detector.

Still further embodiments described herein reference a method of optical sensing, including at least the operations of emitting light toward a measurement site of an object, receiving light exiting a first sub-area of the measurement site, and reflecting light exiting a second sub-area of the measurement site back into the measurement site.

BRIEF DESCRIPTION OF THE DRAWINGS

Reference will now be made to representative embodiments illustrated in the accompanying figures. It should be understood that the following descriptions are not intended to limit the disclosure to one preferred embodiment. To the contrary, each is intended to cover alternatives, modifications, and equivalents as may be included within the spirit and scope of the described embodiments and as defined by the appended claims.

FIG. 6A depicts a bottom surface of an example electronic device with another reflector adapted for use with an optical sensing system.

FIG. 6B depicts a bottom surface of an example electronic device with another reflector adapted for use with an optical sensing system.

The use of the same or similar reference numerals in different drawings indicates similar, related, or identical items.

Figures 1A, 1B:
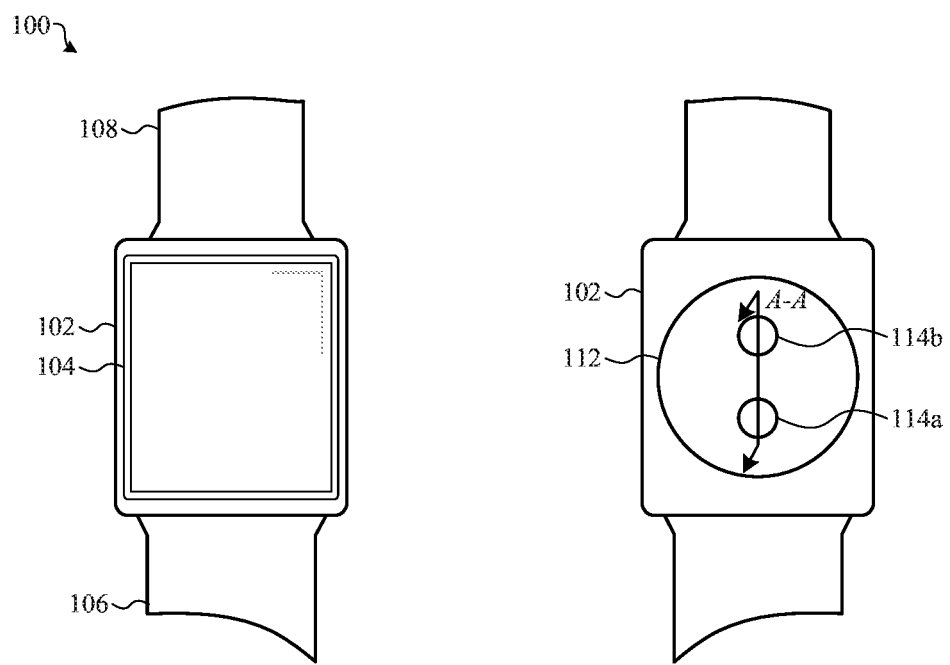
FIG. 1A depicts a top plan view of an example electronic device.
FIG. 1B depicts a bottom plan view of the example electronic device of FIG. 1A, showing separated apertures associated with an optical sensing system defined within a bottom surface of the example electronic device.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

Embodiments described herein reference systems and methods for increasing the speed, sensitivity, accuracy, precision, and/or reliability of optical sensing systems configured for use with small form factor electronic devices, such as wearable devices, although the various systems and methods described herein are not limited to particular form factors and can apply equally to larger embodiments. Further, it should be appreciated that the various embodiments described herein, as well as the functionality, operation, components, and capabilities thereof may be combined with other elements as necessary, and so any physical, functional, or operational discussion of any element, feature, structure, or interrelation is not intended to be limited solely to a particular embodiment to the exclusion of others. Moreover, although many embodiments described herein reference optical sensing systems configured to provide functionality such as fitness or health tracking or physiological data collection to a wearable electronic device, one may appreciate that the various systems and methods described herein are not limited to use of optical sensing systems in this manner. In other words, the various optical sensing systems as described herein (and methods associated therewith) can be used to detect, sense, or quantify other biological or non-biological properties of a user, another biological subject, a non-biological object or surface, or for any other purpose. For example, an optical sensing system can be used to detect subsurface characteristics of a material during a manufacturing process to determine whether the material should be rejected or accepted. In another example, an optical sensing system can be disposed onto or into a veterinary or medical diagnostic tool (e.g., wand, pen, etc.) that can be placed against a patient's skin in order to obtain physiological characteristics of said patient. Such a medical diagnostic tool can be used, in one example, with multiple patients in an emergency setting to assist veterinary or medical professionals with triage decisions.

Many embodiments described herein reference an optical sensing system disposed below a convex surface defining two apertures symmetrically spaced about the principal axis of the curve. A light emitter of the optical sensing system can be positioned behind one aperture and a light detector of the optical sensing system can be positioned behind the other aperture. In this manner, when the optical sensing system is placed in contact with a measurement site, the light emitter and the light detector can be optically isolated from one another by the apex of the convex curvature.

More particularly, because the apex of the convex curvature is the portion of the surface extending outwardly the farthest, the apex will contact the surface of a prospective measurement site first, thereby forming an opaque boundary with the measurement site that optically partitions the illumination area from the collection area. In these embodiments, the quantity of light exiting the collection area after being affected by the characteristics of the subsurface of the measurement site (hereinafter the "subsurface-affected light") may be greater than the quantity of light reflecting directly from the surface of the measurement site (hereinafter the "surface-reflected light") because surface-reflected light may be substantially or entirely blocked by the optical barrier established by the convex curvature of the surface.

Further embodiments can incorporate an optically reflective material disposed on, within, or adjacent to the apertures defined by the convex surface. In these embodiments, the optically reflective material can be disposed about the perimeter of the apertures respectively associated with the light emitter and the light detector of the optical sensing system. More particularly, the optically reflective material may be disposed and oriented to reflect light onto or into the measurement site. In this manner, both surface-reflected light and subsurface-affected light that exits the measurement site outside of the collection area can be reflected back into the measurement site (hereinafter the "recovered light"), thereby increasing the quantity of subsurface-affected light received by the light detector.

In one non-limiting alternative phrasing, these embodiments can incorporate reflective materials so as to direct as much light as possible into the subsurface of the measurement site so that said light, via specular or diffuse reflection, may have one or more additional chances to be reflected toward the collection area. Thus, in these embodiments, the quantity of subsurface-affected light received by the light detector of the optical sensing system may be greater than the quantity of subsurface-affected light received by the light detector of embodiments omitting said reflective material.

Optical sensing system embodiments described herein can exceed the performance of conventional optical sensing systems unable to discriminate between surface-reflected light and subsurface-affected light while orienting the light emitter and light detector to face the same surface. Particularly, in many conventional examples, the quantity of surface-reflected light received by a light detector may predominate the quantity of subsurface-affected light received by the same. As a result, many conventional optical sensing systems require a substantial amount of data over a substantial period of time in order to account for the effects of noise and to detect and quantify characteristics of the measurement site.

Conversely, an electronic device incorporating optical sensing systems as described herein may quantify surface and/or subsurface characteristics of a measurement site onto which the electronic device is placed with increased speed, accuracy, and precision.

Example electronic devices that can incorporate optical sensing systems as described herein can include, but are not limited to, a telephone, a headset, a pulse oximeter, a digital media player, a tablet computing device, a laptop computer, a desktop computer, a timekeeping device, a peripheral input device (e.g., keyboard, mouse, trackpad), a sports accessory device, a wearable device, a medical diagnostic device, a biometric authentication device, and so on.

For example, in one embodiment, an electronic device incorporating an optical sensing system in accordance with embodiments described herein can be worn by a user so as to obtain physiological data from the user such as, but not limited to, heart rate data, blood pressure data, temperature data, oxygen level data, and so on. The wearable electronic device incorporating such an optical sensing system can provide to the user, or a third party authorized by the user, diet or nutrition information, medical reminders, physiological tips or information, or other raw or processed physiological data.

In these embodiments, the optical sensing system may be included within a housing that encloses the internal components of the wearable electronic device. In another example, an optical sensing system may be partially or entirely separate from the wearable electronic device. In these examples, the wearable electronic device can include one or more communication channels, either wired or wireless, to facilitate communication with the external optical sensing system.

In addition to the optical sensing system, the wearable electronic device can include other sensors or sensor systems configured to obtain physiological data from a user. Example sensors can include, but may not be limited to, movement sensors, orientation sensors, temperature sensors, electrodermal sensors, blood pressure sensors, heart rate sensors, respiration rate sensors, oxygen saturation sensors, plethysmographic sensors, activity sensors, pedometers, blood glucose sensors, body weight sensors, body fat sensors, blood alcohol sensors, dietary sensors, and so on.

As with other embodiments described herein, an optical sensing system incorporated by a wearable electronic device can be implemented with a light emitter and a light detector. As noted above, the optical sensing system can be configured to measure changes in the light reflected from a measurement site, such as a wrist of a user.

As used herein, the phrases "reflected from a measurement site" and "exiting a measurement site" (in addition to similar phrases or terminology) generally refer to both surface-reflected light and to subsurface-affected light that originated from a light emitter and, via specular or diffuse reflection from the surface or subsurface of the measurement site, have become oriented to propagate away from the measurement site.

More particularly, the optical sensing system of a wearable electronic device can orient a light emitter to illuminate a portion of the user's wrist. As noted above, this portion of a measurement site is generally referred to herein as "the illumination area." The optical sensing system can also orient the light detector to receive light exiting a separate portion of the user's wrist. As noted above, this portion of the measurement site is generally referred to herein as "the collection area."

In some cases, light from the light emitter may be reflected (specularly and/or diffusely) by the surface of the user's wrist. As noted above, this light is generally referred to herein as "the surface-reflected light." In other cases, light from the light emitter can penetrate the surface of the user's wrist and can be absorbed or reflected (specularly or diffusely) by the subsurface of the wrist. As noted above, this light is generally referred to herein as "the subsurface-affected light." In many cases, the amount of absorption or reflection provided by a particular measurement site at a particular time may depend upon the characteristics of the measurement site at that time. In other words, surface-reflected light may vary predictably with the characteristics of the surface of the measurement site and, similarly, subsurface-affected light may vary predictably with the characteristics of the subsurface of the measurement site.

For example, the tissue of the user's wrist can absorb or reflect light differently depending on physiological characteristics of the surface (e.g., skin, hair, sweat) or subsurface (e.g., stratum corneum of the skin, dermis, blood vessels beneath the skin, and so on) of the user's wrist. For example, sweat on the user's wrist can affect the quantity or quality of surface-reflected light.

In another example, a user's heartbeat can affect the quantity or quality of subsurface-affected light received by the light detector. More particularly, the user's heartbeat can affect an increase or decrease in the user's blood volume within the user's wrist. This periodic distention and contraction is commonly referred to as the user's pulse. As a direct result of changes in the volume of blood proximate to the measurement site, the light absorption capacity of the measurement site may correspondingly increase or decrease which, in turn, can cause the amount of subsurface-affected light received by the light detector to increase and decrease with the user's pulse. This type of volumetric data collection via optical sensing is conventionally referred to as photoplethysmographic data collection (hereinafter "PPG").

As noted above, the light detector of an optical sensing system can receive light exiting the collection area and generate electrical signals corresponding thereto. In certain embodiments, light exiting the collection area can include a component corresponding to surface-reflected light and a component corresponding to subsurface-affected light. In certain embodiments implementing an optical barrier between the light emitter and light detector (e.g., the apex of a concave surface associated with the optical sensing system), the component corresponding to the surface-reflected light can be substantially reduced or eliminated. In these embodiments, the electrical signals generated by the light detector may correspond substantially only to subsurface-affected light.

In many embodiments, the electrical signals generated by the light detector of the optical sensing system can be conveyed as data to the wearable electronic device which, in turn, can utilize the data to quantify one or more physiological characteristics of the user at that time. In many examples, data from the light detector can include information about the collected light such as the chromaticity, brightness, frequency, and/or luminance of the light.

Optical sensing systems as described herein can also be used to obtain non-physiological information or data. For example, the wearable electronic device can use the optical sensing system as a surface audio sensor (e.g., microphone). In other examples, a wearable electronic device can use the optical sensing system as an input device (e.g., wrist-tap input). In still further embodiments, the wearable electronic device can use an optical sensing system to determine a state of the electronic device (e.g., connected to a user, connected to a charger, sitting on a surface such as a table, and so on). In another example, an optical sensing system can be used as a liveness verification for biometric authentication or security embodiments.

Accordingly, optical sensing systems incorporated by embodiments described herein may serve as multi-purpose sensors.

These and other embodiments are discussed below with reference to FIGS. 1A-7. However, those skilled in the art will readily appreciate that the detailed description given herein with respect to these Figures is for explanatory purposes only and should not be construed as limiting.

FIG. 1A depicts a top plan view of an example wearable electronic device 100. In the illustrated embodiment, the wearable electronic device 100 may be implemented as a portable electronic device that is adapted to be worn by a user such as a smart watch. Other embodiments can implement the wearable electronic device 100 differently. For example, the wearable electronic device 100 can be a smart phone, a gaming device, a digital music player, a sports accessory device, a medical device, a device that provides time and/or weather information, a fitness device, and other types of electronic devices suitable for attaching to a user.

The wearable electronic device can be implemented as a fitness device that provides physiological information (whether real-time or not) to the user, authorized third parties, and/or an associated monitoring device. The wearable fitness device may be configured to provide physiological information or data such as, but not limited to, heart rate data, blood pressure data, temperature data, blood oxygen saturation level data, diet/nutrition information, medical reminders, physiological tips or information, or other physiological data. The associated monitoring device may be, for example, a tablet computing device, a phone device, a personal digital assistant, computer, and so on.

The wearable electronic device 100 can be configured in the form of a wearable communications device. A wearable communications device may include a processor coupled with or in communication with a memory, one or more sensors, one or more communication interfaces, output devices such as displays and speakers, one or more input devices, and a fitness or health tracking system. The communication interfaces can provide electronic communications between the communications device and any external communication network, device or platform, such as but not limited to wireless interfaces, Bluetooth interfaces, universal serial bus interfaces, Wi-Fi interfaces, TCP/IP interfaces, network communications interfaces, or any conventional communication interfaces. The wearable communications device may provide information regarding time, health, statuses of externally connected or communicating devices and/or software executing on such devices, messages, video, operating commands, and so forth (and may receive any of the foregoing from an external device), in addition to communications. For simplicity of illustration, the wearable electronic device 100 is depicted in FIG. 1A without many of these elements, each of which may be included, partially, optionally, or entirely, within a housing 102.

The housing 102 can be configured to, at least partially, surround a display 104. In many examples, the display 104 may incorporate an input device configured to receive touch input, force input, and the like and/or may be configured to output information to a user, such as various health parameters or physiological suggestions. The display 104 can be implemented with any suitable technology, including, but not limited to, a multi-touch or multi-force sensing touchscreen that uses liquid crystal display (LCD) technology, light emitting diode (LED) technology, organic light-emitting display (OLED) technology, organic electroluminescence (OEL) technology, or another type of display technology. A button (not shown) might take the form of a home button, which may be a mechanical button, a soft button (e.g., a button that does not physically move but still accepts inputs), an icon or image on the display 104 or on an input region, and so on. Other buttons or mechanisms can be used as input/output devices, such as a speaker, a rotary input device, a microphone, an on/off button, a mute button, or a sleep button.

Additionally, the housing 102 can form an outer surface or partial outer surface and protective case for the internal components of the wearable electronic device 100. In the illustrated embodiment, the housing 102 is formed into a substantially rectangular shape, although this configuration is not required.

The housing 102 can be formed of one or more components operably connected together, such as a front piece and a back piece or a top clamshell and a bottom clamshell. Alternatively, the housing 102 can be formed of a single piece (e.g., uniform body or unibody). The housing 102 can be coupled to a coupling mechanism used to attach to a user. For example, as illustrated, the housing 102 can be coupled to a band suitable for attaching to a user's wrist. The band can include a first band portion 106 and a second band portion 108. The first band portion 106 can be configured to join with or couple to the second band portion 108 around the user's wrist, thereby removably attaching the wearable electronic device 100 to the user. The wearable electronic device 100 may include one or more sensors configured to obtain physiological information or data from a user. In some cases, these sensors can be configured to operate via non-invasive optical sensing. In such an embodiment, one or more optical sensors configured for obtaining health-related and/or physiological information from a user can be disposed adjacent to a bottom surface of the housing 102.

FIG. 1B depicts a bottom plan view of the wearable electronic device of FIG. 1A, showing two sensor windows 114a, 114b associated with an optical sensing system. In many cases, an optical sensing system can be a distributed system such that one portion of the optical sensing system is positioned proximate to one of the two sensor windows 114a, 114b whereas another portion of the optical sensing system is positioned proximate to another of the two sensor windows 114a, 114b. In still further embodiments, an optical sensing system can be disposed proximate to a single sensor window. In still further embodiments, an optical sensing system can be disposed proximate to more than two sensor windows. In still further examples, an optical sensing system can be disposed in another manner that incorporates the optical sensing system within an optical circuit that includes a measurement site or a measurement subject.

Figure 2A:
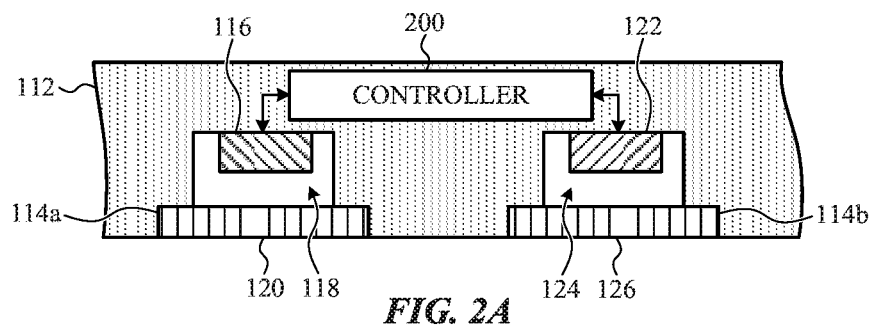
FIG. 2A depicts a simplified cross-section view of a light emitter and a light detector of an optical sensing system taken through section A-A of FIG. 1B.

An optical sensing system can include a light emitter and a light detector (not shown in FIG. 1B, see, e.g., FIG. 2A). In many embodiments, the light emitter can be configured to illuminate a portion of a measurement site and a light detector can be configured to receive light exiting the measurement site. In these examples, the light emitter can be a light emitting diode and the light detector can be a photodiode, phototransistor, and/or an optical image sensor. In other embodiments, a light emitter and a light detector can be formed from the same material and/or may be formed as the same component, such as a phototransistor. In these examples, the light emitter and light detector can each operate as the other element. Accordingly, for certain embodiments described herein, a light emitter may be operable to function as a light emitter in a first mode (e.g., light emitting mode) and also operable to function as a light detector in a second mode (e.g., light receiving mode). Similarly, a light detector may be operable to function as a light detector in a first mode (e.g., light receiving mode) and also operable to function as a light emitter in a second mode (e.g., light emitting mode). The light emitter and the light detector of the optical sensing system are not shown in FIG. 1B for simplicity of illustration, although it may be understood that the light emitter and the light detector can be disposed entirely or partially within the housing of the wearable electronic device 100.

By monitoring the output from the light detector of the optical sensing system, the wearable electronic device 100 can quantify physiological information related to the measurement site or related to the user of the wearable electronic device 100.

For one non-limiting example, the light emitter of the optical sensing system of the wearable electronic device 100 can be configured to emit green light toward the skin of the user's wrist. Some of the light may be reflected by the skin and some of the light may penetrate the skin. A portion of the penetrating light may be absorbed while another portion of the penetrating light can be reflected, exit the wrist, and return toward the wearable electronic device 100 (e.g., subsurface-affected light). The green light exiting the skin of the wrist can be received by the light detector and correlated to physiological properties of the subsurface of the user or the user's wrist. For example, a small amount of green light received by the light detector may correspond to a high amount of absorption which, in turn, may indicate a high volume of blood within blood vessels below the skin, which in turn may correspond to an ejection portion (e.g., higher blood pressure) of the user's cardiac cycle.

In many embodiments, the light emitted by the light emitter may be specifically regulated (hereinafter the "modulated light"). For example, light emitted by the light emitter can have a selected frequency, amplitude, color, direction, and/or modulation pattern. In these embodiments, the light received by the light detector can be demodulated prior to further signal processing (hereinafter the "demodulated light"), thereby attenuating or eliminating the components of the signal from the light detector associated with interference (e.g., noise).

In many embodiments, the light emitter can be disposed adjacent to a sensor window 114a and the light detector can be disposed adjacent to a second window 114b. In some embodiments, the light emitter may be positioned within the housing behind the first sensor window 114a and the light detector may be positioned within the housing behind the sensor window 114b. In many cases, the sensor windows 114a, 114b can be formed from optically-transparent lenses or covers that are disposed above the light emitter and light detector within apertures defined within the bottom surface 112.

As used herein, the term "optically transparent" and variants thereof does not necessarily mean that the referent structure is transparent to all visible or invisible light. Instead, the phrase is generally used to indicate transparency or translucency to the particular wavelength of light emitted by the light emitter and/or received by the light detector for a particular embodiment. Thus, some optically transparent sensor windows may be substantially transparent to infrared light while blocking visible light. In other examples, some optically transparent sensor windows may be substantially transparent to a particular wavelength of visible light while blocking other frequency bands of visible light. In other embodiments, some optically transparent sensor windows may have electrically or thermally variable transparency or opacity. For example, some embodiments can include sensor windows with a liquid crystal diode layer positioned between one or more polarizers. In these examples, the optically transparent sensor window can be optically transparent in a first mode and optically opaque (or substantially opaque) in a second mode.

In some embodiments, the sensor windows 114a, 114b can cooperate with the bottom surface 112 of the housing 102 to form a convex shape. In these examples, the sensor windows 114a, 114b may be separated from one another, disposed symmetrically (or asymmetrically) about the principal axis of the convex curvature of the bottom surface 112.

In these embodiments, the bottom surface 112 can curve outwardly from the housing 102, defined by a particular radius of curvature. In some examples, the sensor windows 114a, 114b can be disposed such that the central axis of each respective sensor window is perpendicular to a plane tangent to the curvature of the bottom surface 112. In other words, each sensor window can be oriented at an angle from the principal axis of the curvature of the bottom surface 112 such that the external surface of each sensor window forms a substantially continuous surface with the portions of the bottom surface 112 adjacent thereto (see, e.g., FIG. 3C).

In some examples, the light emitter and light detector can be oriented to be parallel to the axis through the center of each respective sensor window. In other words, the light emitter may be configured to emit light parallel to the axis through the center of the sensor window 114a and the light detector may be configured to receive light directed parallel to the axis through the center of the sensor window 114b. In other examples, the light emitter and light detector can be oriented to be parallel to one another. In these embodiments, the light emitter can be oriented to emit light in a direction parallel to the principal axis of the convex curvature and the light detector may be configured to receive light directed parallel to the principal axis of the convex curvature.

In some embodiments, the sensor windows 114a, 114b can take a shape that is discontinuous with the shape of the bottom surface 112. For example, the sensor windows 114a, 144b protrude from or depress into the bottom surface 112 in a manner that breaks the continuity of the shape of the bottom surface 112. In other examples, the sensor windows 114a, 114b can be substantially flat. In till other examples, the sensor windows 114a, 114b, can take a concave and/or convex shape so as to protrude from or depress into the bottom surface 112. In other embodiments, the sensor windows 114a, 114b can take a different shape.

Figure 3A:
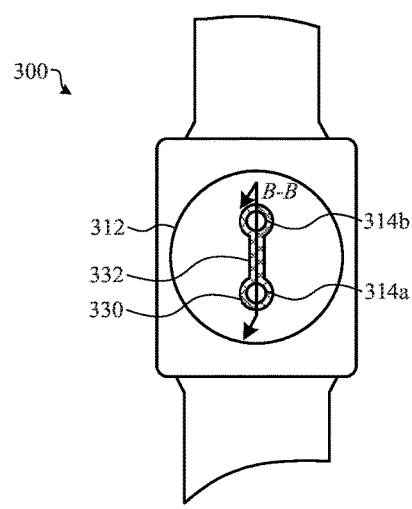
FIG. 3A depicts a bottom plan view of a wearable electronic device showing an optical sensing system implemented with one example of a reflector.
Figure 3B:
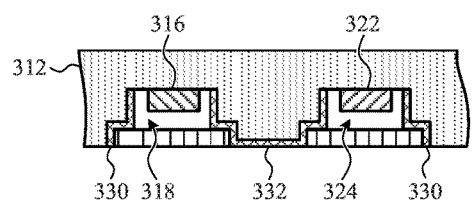
FIG. 3B depicts an example cross-section of FIG. 3A taken through section B-B, showing a simplified view of the optical sensing system of FIG. 3A.
Figure 3C:
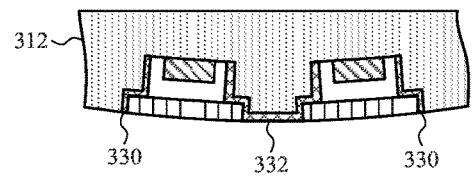
FIG. 3C depicts an alternative example simplified cross-section of FIG. 3A taken through section B-B, showing a simplified view of the optical sensing system of FIG. 3A implemented with a bottom surface having a convex curvature.

In these embodiments, the curvature of the housing itself can provide an optical barrier between the light emitter and the light detector (see, e.g., FIG. 3C). The optical barrier between the light emitter and the light detector can improve the performance of the optical sensing system by reducing the amount of surface-reflected light received by the light detector.

More specifically, in many embodiments, the apex of the convex curvature of the bottom surface 112 can physically and optically separate the light emitter from the light detector when the wearable electronic device 100 is positioned on a measurement site. In other words, the portion of the bottom surface 112 extending outwardly the farthest (which will contact the measurement site first) will ensure optical separation between the light emitter and light detector. In this manner, any modulated light received by the light detector will have either passed through the measurement site (e.g., subsurface-affected light) or will result from an external source (e.g., hereinafter the "external noise"). As noted above, external noise can be effectively mitigated or eliminated via demodulation of the light received by the light detector.

Thus, absent an optical barrier between the light emitter and the light detector, the light detector can receive both modulated surface-reflected light and modulated subsurface-affected light. As noted above, modulated surface-reflected light can predominate modulated subsurface-affected light which, in turn, can cause physiological characteristics of the subsurface to be substantially obscured, distorted, or otherwise concealed.

Accordingly, many embodiments described herein implement a selected radius of curvature of the bottom surface 112 so as to reduce the amount of surface-reflected light received by the light detector and to increase the amount of subsurface-affected light received by the light detector. For example, the greater the radius of curvature of the bottom surface 112, the greater the angle between the axis of the sensor window 114a and the axis of the sensor window 114b may become. In some embodiments, the convex curvature of the bottom surface 112 can take a substantially spherical convex shape. In other embodiments, the convex curvature of the bottom surface 112 can take a parabolic convex shape.

In many embodiments, and as illustrated, the sensor windows 114a, 114b can be separated by a selected distance either symmetrically or asymmetrically about the apex of the convex curvature of the bottom surface 112. In other examples, the sensor windows 114a, 114b can be disposed in other locations.

For example, in embodiments implemented with closely-spaced (e.g., adjacent to the apex of the convex curvature) sensor windows, the quantity of light lost to absorption within the measurement site can decrease thereby increasing the quantity of subsurface-affected light received. On the other hand, for closely-spaced sensor windows, the quantity of surface-reflected light may also increase as a result of the relative proximity of the light emitter and the light detector.

Conversely, in examples implemented with sensor windows spaced a greater distance apart (e.g., closer toward the perimeter of the bottom surface 112), the quantity of light lost to absorption within the measurement site may increase, potentially decreasing the quantity of subsurface-affected light received. However, the quantity of surface-reflected light may also decrease.

In a non-limiting alternate phrasing of the considerations presented above, the measurement site may appear more brightly illuminated to the light detector if the sensor windows 114a, 114b are sufficiently close to one another, but may appear too dimly illuminated if the sensor windows 114a, 114b are positioned too far apart. Similarly, the light detector may collect a greater proportion of light corresponding only to subsurface events if the sensor windows 114a, 114b are sufficiently far apart, but the light emitter may emit too much light for the light detector to detect subsurface events if the sensor windows 114a, 114b are too close together.

Accordingly, the distance separating the sensor windows 114a, 114b may vary from embodiment to embodiment and may depend upon the output capacity of the light emitter, the sensitivity of the light detector, the modulation pattern or scheme associated with the optical sensing system, and/or the characteristics of the measurement site. Alternatively or additionally, the output of the light emitter, the sensitivity of the light detector, and/or the modulation pattern or scheme used by the optical sensing system can each be selected based, in part, upon the distance separating the sensor windows 114a, 114b, the locations of which may be fixed or influenced by the layout of components, certain manufacturing tolerances, certain material selections, certain assembly considerations, certain aesthetic preferences, and so on.

In many embodiments, the distance separating the sensor windows 114a, 114b (and, correspondingly the distance separating the light emitter and light detector) can be defined by the placement of apertures within the housing of the wearable electronic device 100. For example, as illustrated, the sensor windows 114a, 114b can be disposed within circular apertures defined within the bottom surface 112, each centered approximately half a radius length from the center of the bottom surface 112.

Furthermore, although many embodiments are described herein with reference to optical sensors disposed within axially-symmetric convexly-curved surfaces, such a configuration may not be required of all embodiments. For example, in other embodiments, the bottom surface 112 of the wearable electronic device 100 can be formed to take the shape of a pitched roof. In another embodiment, the bottom surface 112 can be formed to take the shape of an arch. In other embodiments, the bottom surface 112 can include a protrusion that physically separates the sensor windows. In still further examples, the bottom surface 112 can be flat, faceted, or concave. In further embodiments, the bottom surface 112 can take an arbitrary shape. In other embodiments, the sensor windows 114a, 114b can be disposed within a convexly curved bottom surface without being oriented to follow the curve thereof. In other words, the sensor windows 114a, 114b can be disposed so as to be parallel to the principal axis of the curvature of the bottom surface 112.

FIG. 2A depicts a simplified cross-section of FIG. 1B taken through section A-A, showing a simplified view of the optical sensing system of FIG. 1B. The optical sensing system includes a light emitter 116 and a light detector 122 both coupled to a controller 200. In many examples, the controller 200 can be implemented as a processor, a digital circuit, an analog circuit, or any combination thereof, that is configured to perform and/or coordinate one or more operations of the optical sensing system or the wearable electronic device 100. In one embodiment, the controller 200 can be coupled to a processor associated with the wearable electronic device 100. In another embodiment, the controller 200 can be a processor associated with the wearable electronic device 100 such that the controller 200 is configured to perform and/or coordinate the interoperation of the various components of the wearable electronic device 100 such as, but not limited to, driving a display, receiving input from a touch or force sensor, receiving input from a button or rotary dial, communicating with other electronic devices via a communication channel, distributing power from a battery, and so on.

In one embodiment the light emitter 116 may be a light emitting diode configured to emit light at a particular frequency. For example, in certain embodiments the light emitter 116 can be configured to emit green light. In another example, the light emitter 116 can emit infrared light. In still further examples, the light emitter 116 can be configured to emit light in another frequency band.

The light detector 122 can be a photodiode, phototransistor, and/or an optical image sensor such as a charge-coupled device ("CCD") or complementary metal-oxide semiconductor ("CMOS") array.

The light emitter 116 can be disposed within the housing of the wearable electronic device and can be positioned below the sensor window 114a. In one example, the light emitter 116 can be disposed within a cavity 118 defined within the housing of the wearable electronic device. In these examples, the cavity 118 can be defined by the housing such that the cavity 118 is axially aligned with the central axis of the sensor window 114a. In many cases, the interior of the cavity 118 can be painted with a reflective surface treatment. In some embodiments, the cavity 118 may have a shorter width than that of the sensor window 114a so as to form a shelf therewith, although this configuration is not required. In some examples, the cavity 118 can be filled with a filler material. In some examples, the filler material can be optically transparent. In other examples, the filler material can be optically diffusive.

A lens 120 or window may seal the cavity 118; the lens 120 need not focus or scatter light in any particular fashion. The lens 120 may be formed from the same material as the bottom surface 112, although this is not required. In one embodiment, the lens 120 can be configured to diffuse light, while in other embodiments it may focus light or may not affect the directionality of light passing therethrough. In some embodiments, the lens 120 may be optically transparent. In still further embodiments, the lens 120 may be configured to exhibit transparency in a first frequency band of light and to be opaque in a second frequency band of light. For one example, the first frequency band of light can be infrared light and the second frequency band of light can be visible light.

As with the light emitter 116, the light detector 122 can be disposed within the housing of the wearable electronic device and can be positioned below the sensor window 114b. In one example, the light detector 122 can be disposed within a cavity 124 defined within the housing of the wearable electronic device. As with the cavity 118, the cavity 124 can be defined by the housing such that the cavity 124 is axially aligned with the central axis of the sensor window 114b. In many cases, the interior of the cavity 124 can be painted with a reflective surface treatment. In many examples, the cavity 124 can be sealed with a lens 126.

As with the lens 120, the lens 126 can be configured to diffuse light. In other embodiments, the lens 126 may be optically transparent, or may be shaped to focus light to a particular focal point. In still further embodiments, the lens 126 may be configured to exhibit transparency in a first frequency band of light and to be opaque in a second frequency band of light. For one example, the first frequency band of light can be infrared light and the second frequency band of light can be visible light.

Figure 2B:
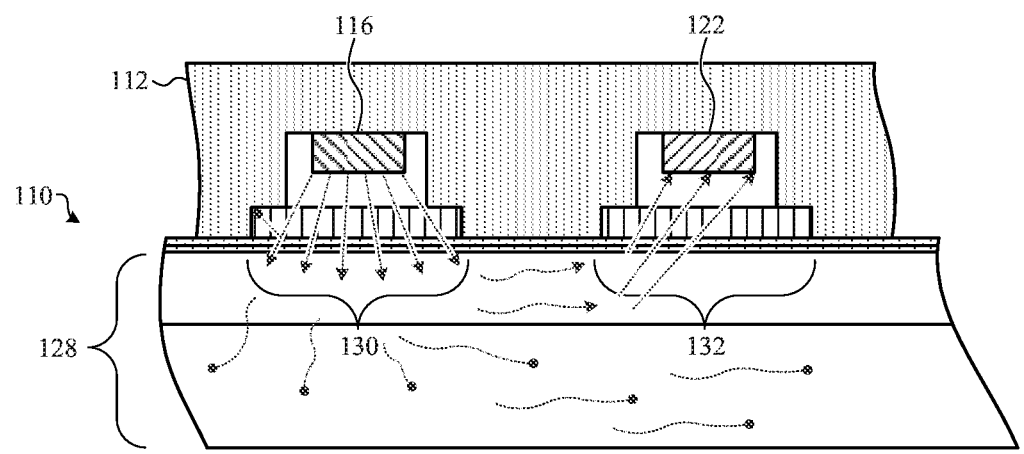
FIG. 2B depicts the simplified cross-section view of FIG. 2A, showing a set of example light reflection and absorption paths from the light emitter, through a measurement site of a subject, to the light detector of the optical sensing system.

FIG. 2B depicts a second cross-section like that of FIG. 2A, now showing a set of example light paths from a light emitter through a measurement site 110 of a subject to a light detector of the optical sensing system. As illustrated, light emitted from the light emitter 116 passes into an illumination area 130 of the measurement site 110, through an intermediate volume 128 of the measurement site 110, to a collection area 132 of the measurement site 110, and, thereafter, exits the collection area 132 where it may be collected by the light detector 122 and conveyed to the wearable electronic device 100 via the controller 200 (not shown). In many embodiments, the subject may be a human user. As illustrated, point-terminated light vectors represent light absorbed by the measurement site or another material. Similarly, arrow-terminated light vectors represent light reflected either specularly or diffusely.

As illustrated, a portion of the light emitted from the light emitter 116 may not exit the intermediate volume 128 through the collection area 132. For example, some light may continue transmitting in a direction parallel to the length of the intermediate volume 128. In addition, some light can transmit in directions away from the collection area 132. In addition, some light can be absorbed within the intermediate volume, depicted in FIG. 2B as point-terminated lines. Accordingly, the quantity of light received by the light detector 122 may be less than the quantity of light emitted by the light emitter 116.

FIG. 3A depicts a bottom plan view of a wearable electronic device 300 showing an optical sensing system having reflective surface treatments. As with the embodiment depicted in FIG. 2A, the wearable electronic device 300 can include two separated sensor windows 314a, 314b associated with a light emitter and a light detector of an optical sensing system, respectively. In addition, the wearable electronic device 300 can include a reflector 330 that surrounds the sensor windows 314a, 314b. The reflector 330 can also include an extended portion 332 that extends toward the sensor window 314b from the sensor window 314a. The extended portion 332 can provide a reflective surface to the entire area between the sensor windows 314a, 314b. It should be appreciated that various embodiments may have more or fewer apertures, more or fewer light emitters and more or fewer light detectors.

In many examples, and as illustrated in FIG. 3A, the reflector 330 can be disposed on an outer surface of the bottom surface 312. In these examples, the reflector 330 can be disposed onto the bottom surface 312 via an adhesive. In another embodiment, the reflector(s) and/or reflective surface(s) can be disposed onto the bottom surface 312 via another means such as vapor deposition, laser etching, pressure bonding, welding, and so on.

In still further embodiments the reflector(s) and/or reflective surface(s) can be disposed below the outermost surface of the bottom surface 312. For example, in some cases, the bottom surface 312 can be formed from a laminate material. In these examples, the reflector(s) and/or reflective surface(s) can be intestinally disposed between layers of the laminate material.

In still other examples, the reflector(s) and/or reflective surface(s) can be disposed onto or into the sensor windows 314a, 314b. For example, in one embodiment, the reflector 330 can be disposed onto an outer surface about the perimeter of the sensor windows 314a, 314b. In another example, the reflector 330 can additionally or separately be disposed onto a sidewall of the sensor windows 314a, 314b. In another example, the reflector 330 can be additionally or separately disposed onto a sidewall of a cavity and/or aperture defined within the bottom surface 312. In still further embodiments, the reflector 330 can be disposed onto, attached to, or adhered to other portions of the bottom surface 312, the sensor windows 314a, 314b, or any other portion of the wearable electronic device 300 suitable for reflecting light back into a measurement site.

In still further embodiments, the reflector 330 can be oriented to reflect light in a particular direction. For example, the reflector 330 disposed most adjacent to the sensor window 314a can be positioned, oriented, disposed, or configured to reflect light generally toward the sensor window 314b. Similarly, the reflector 330 disposed most adjacent to the sensor window 314b can be positioned, oriented, disposed, or configured to reflect light generally toward a center point of the sensor window 314b. In this manner, various areas of the reflector 330 can be configured to reflect light in different directions. In many cases, the different directions that different areas of the reflector 330 are configured to reflect toward may be selected, at least in part, on the positioning of a light emitter and a light detector of an optical sensing system with which the reflector 330 is associated. More particularly, many embodiments can configure the reflector 330 to reflect light generally toward a light detector of an optical sensing system.

As noted with respect to other embodiments described herein, the reflector 330 and the extended portion 332 can be formed from any suitable optically reflective material such as glass, crystal, sapphire, zirconia, metals, and so on. In certain embodiments, the reflective surface can be configured to be optically transparent in one frequency band of light and optically reflective in another frequency band of light. As a non-limiting example, the reflector 330 may be configured to reflect infrared light while absorbing red light. In other examples, the reflector 330 can be configured to reflect more than one frequency band of light. For example, certain embodiments may include a configuration in which the reflective surface reflects green light and infrared light while substantially absorbing all other frequencies of light.

FIG. 3B depicts a simplified cross-section of FIG. 3A taken through section B-B, showing a simplified view of the optical sensing system of FIG. 3A. As with the embodiment depicted in FIGS. 2A-2B, the optical sensing system includes a light emitter 316 and a light detector 322. In one embodiment the light emitter 316 may be a light emitting diode configured to emit light at a particular frequency. For example, in certain embodiments, the light emitter 316 can be configured to emit green light. In another example, the light emitter 316 can emit infrared light. In still further examples, the light emitter 316 can be configured to emit light in another frequency band of light.

The light emitter 316 can be disposed adjacent to a cavity 318 that extends toward the sensor window 314a. In some embodiments, the cavity 318 may have a shorter width than that of the sensor window 314a, although this configuration is not required. The cavity 318 can be sealed with a lens that, in certain embodiments, may be either optically diffusive or optically transmissive.

As with the light emitter 316, the light detector 322 can be disposed adjacent to a cavity 324 and below a lens that, in certain embodiments, may be either optically diffusive or optically transmissive.

The depicted embodiment also includes a reflective coating or surface 330 (collectively, the "reflective surface"), which, as illustrated, may contour to the geometry of the sensor windows 314a, 314b and the cavities 318, 324. In one embodiment, the bottom surface 312 can take a substantially flat shape such as shown in FIG. 3B. In other embodiments, the bottom surface 312 can take a substantially convex shape such as shown in FIG. 3C.

Figure 3D:
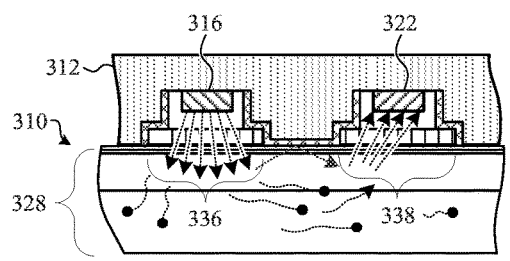
FIG. 3D depicts the simplified cross-section of FIG. 3A, showing a set of example light reflection and absorption paths from a light emitter, through a measurement site of a subject, to a light detector of the optical sensing system of FIG. 3A.

Independent of shape, the reflector 330 can serve the dual purpose of providing a reflector for both the light emitter 316 and the light detector 322 while also providing a reflective surface to redirect light exiting a measurement site. For example, FIG. 3D depicts the simplified cross-section of FIG. 3B, showing a set of example light paths from a light emitter through a measurement site 310 of a subject to a light detector of the optical sensing system. As illustrated, light emitted from the light emitter 316 passes into an illumination area 336 of the measurement site 310, through an intermediate volume 328 of the measurement site 310, to a collection area 338 of the measurement site 310, and, thereafter, exits the collection area 338 where it may be collected by the light detector 322 and conveyed to the wearable electronic device 300. In some embodiments the reflective surface may be shaped to focus reflected light at a particular point or otherwise shape light exiting or entering the respective cavities.

Figure 3E:
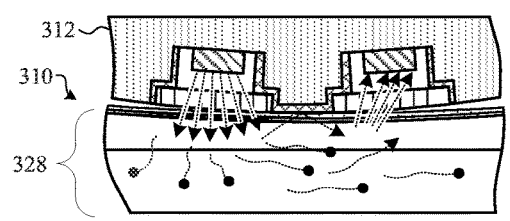
FIG. 3E depicts an alternative example simplified cross-section of FIG. 3A, showing a set of example light absorption and reflection paths from a light emitter, through a measurement site of a subject, to a light detector of the optical sensing system of FIG. 3A implemented with a bottom surface having a convex curvature.

As noted above, in certain embodiments, the bottom surface 312 can take a substantially flat shape such as shown in FIG. 3D. In other embodiments, the bottom surface 312 can take a substantially convex shape such as shown in FIG. 3E.

Additionally, as illustrated, the sensor windows 314a, 314b can be spatially separated by a particular distance.

As with the embodiment depicted in FIG. 2B, a portion of the light emitted from the light emitter 316 may not exit the intermediate volume 328 through the collection area 338. Correspondingly, a greater portion of the light emitted from the light emitter 316 can be reflected by the reflector 330 back into the intermediate volume 328. The recovered light can thereafter be reflected, diffused, or absorbed by the tissue of the intermediate volume 328. In the case that the recovered light is either reflected or diffused by the tissue of the intermediate volume 328, the recovered light may have another opportunity to exit through the collection area 338. In these embodiments, the quantity of light collected by the light detector 322 may be greater than the quantity of light received by the light detector 122 of FIG. 2B.

Similarly, the extended portion 332 of the reflector 330 can reflect light recovered light back into the intermediate volume 328 across the area extending between the sensor windows 314a, 314b. More particularly, the extended portion 332 can guide light exiting the intermediate volume 328 toward the collection area 338 by repeatedly reflecting the light back into the intermediate volume 328.

Figure 4A:
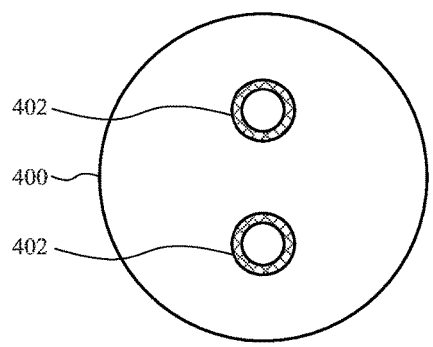
FIG. 4A depicts a bottom surface of an example electronic device with a reflector adapted for use with an optical sensing system.
Figure 4B:
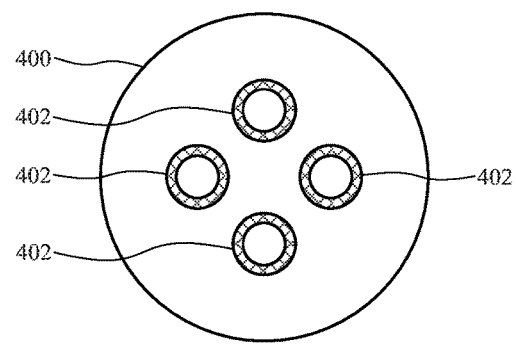
FIG. 4B depicts a bottom surface of an example electronic device with another reflector adapted for use with an optical sensing system.

Other wearable electronic devices may include a reflective surface having different geometry than that shown in FIGS. 3A-3E. For example, FIG. 4A depicts a bottom surface of a wearable electronic device 400 having two separated reflective surfaces 402. In such an example, the reflective surfaces can be formed as rings of reflective material surrounding one or more apertures associated with a light emitter and/or a light detector. In other embodiments, an optical sensing system can include more than one pair of sensor windows associated with more than one light emitter and more than one light detector, such as shown in FIG. 4B. In such an embodiment, a single optical sensing system can include more than one light emitter and more than one light detector. Alternatively, a first optical sensing system can be associated with a first pair of sensor windows and a second optical sensing system can be associated with a second pair of sensor windows.

In one embodiment, a first light emitter can be disposed symmetrically opposite a first light detector (e.g., top and bottom sensor windows as illustrated in FIG. 4B) and a second light emitter can be disposed symmetrically opposite a second light detector (e.g., left and right sensor windows as illustrated in FIG. 4B). In such an embodiment, the first light emitter can be configured to emit light in a first frequency band of light and the second light emitter can be configured to emit light in a second frequency band of light.

For one non-limiting example, the first light can be configured to emit green light whereas the second light emitter can be configured to emit infrared light. Correspondingly, the first and second light detectors can be configured to receive green and infrared light, respectively. In these embodiments, the light emitted from the first light emitter can be modulated differently from the light emitted by the second light emitter. In this manner, the first and second light emitters can operate at substantially the same time without mutually interfering. In other embodiments, the first and second light emitters can be configured to operate in a sequence (e.g., first light emitter active, second light emitter active, first light emitter active, second light emitter active, and so on). In other embodiments, an arbitrary pattern can be used.

In still further embodiments, a single sensor window can be positioned above both a light emitter and a light detector, each associated with a different optical sensing system. For example, the top sensor window as illustrated in FIG. 4B can be positioned above a light emitter that is associated with a light detector positioned below the bottom sensor window of the same figure. In addition, the top sensor window as illustrated in FIG. 4B can also be positioned above a light detector that is associated with a light emitter positioned below the bottom sensor window of the same figure. In this manner, more than one optical sensing system and/or light emitter and detector pair can be disposed below a single sensor window.

In still further embodiments, the first light emitter can be associated with a light detector that is disposed to be axially symmetric thereto. For example, a first light emitter can be configured to operate with a first light detector positioned adjacent to the first light emitter (e.g., top and left sensor windows as illustrated in FIG. 4B). In this manner, multiple measurement sites can be measured with a single optical sensing system. For example, in an embodiment in which each sensor window of FIG. 4B is positioned above both a light emitter and a light detector, twelve possible combinations of light emitter and light detector may be possible (e.g., top emitter with right detector, top emitter with bottom detector, and so on). In still further embodiments, a light emitter can be configured to operate with a light detector disposed below the same sensor window. In these embodiments, four additional measurement areas can be measured in order to obtain additional information about the characteristics of the measurement site.

Figure 5:
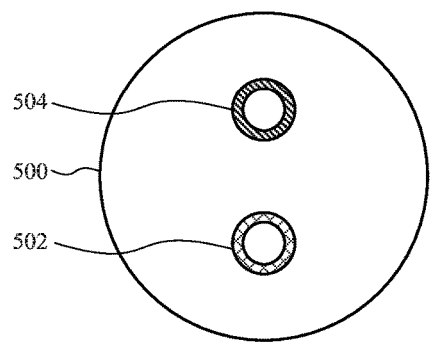
FIG. 5 depicts a bottom surface of an example electronic device with another reflector adapted for use with an optical sensing system.

In other embodiments, reflective surfaces can have different reflective properties. For example, as shown in FIG. 5, a wearable electronic device 505 can include a first reflective surface 502 having a first reflectivity characteristic (e.g., reflecting a certain frequency band, absorbs a certain frequency band, etc.), and a second reflective surface 504 that has a second reflectivity characteristic. In still further embodiments, the entire bottom surface of a fitness or health tracking system may form a reflective surface, such as depicted in FIGS. 6A-6B.

In some embodiments, the bottom surface of the fitness or health tracking system that surrounds apertures provided for sensors within the fitness or health tracking system (e.g., optical sensing systems) can be made from an optically reflective material so as to form a reflective surface, such as depicted in FIG. 6A. In other embodiments, the bottom surface 600 of a wearable electronic device can include a first reflective surface 602 having a first reflectivity characteristic (e.g., reflecting a certain frequency band, absorbs a certain frequency band, etc.), and a second reflective surface 604 that has a second reflectivity characteristic, such as depicted in FIG. 6B. In these embodiments, the first reflective surface 602 can be configured to reflect light within a first frequency band of light and the second reflective surface 604 can be configured to reflect light within a second frequency band of light. In some examples, the first and second reflective surface 602, 604 can be configured to reflect light within overlapping frequency bands of light. For one non-limiting example, both reflective surfaces can be reflective to light within the visible spectrum, while the second reflective surface 604 is transparent to light within the infrared spectrum. In this manner, the bottom surface 600 of the wearable electronic device can appear to a user to form a substantially continuous mirrored surface.

Although many embodiments described herein refer to an optical sensing system having a reflective surface, such a configuration is not required. For example, in certain embodiments, an existing surface of the housing of a wearable electronic device can be coated with a mirror like coating. For example, a polished metal coating may be applied around or between the one or more apertures associated with the optical sensing system. In other examples, a thin metallic layer can be deposited via vapor deposition or another suitable process. More specifically, aluminum or chromium may be deposited via vapor deposition to create a highly reflective surface proximate to or between the one or more apertures associated with the optical system.

In these embodiments, the coating can be applied to the housing of the wearable electronic device or, in the alternative, can be applied in a layered fashion beneath another optically clear layer. More particularly, a coating can be applied to an inside surface of a transparent material (e.g., glass, sapphire, zirconia, etc.). Thereafter, in some embodiments, a subsequent layer may be applied over the coating. In this manner, the coating may be sealed from environments to which the wearable electronic device may be exposed.

In other examples, the reflective surface may be formed from a material that is reflective to infrared light but absorbs visible wavelengths. In these examples, a reflective coating may appear as a darkened or otherwise opaque area that may be cosmetically indistinguishable from other portions of the housing of the wearable electronic device.

In still further examples, the reflective surface may utilize or exploit diffuse reflectivity. More particularly, the reflective surface may be formed from a material that diffuses light. In one example, an optically white ink layer can be applied proximate to or between the one or more apertures associated with the optical sensing system. In these embodiments, the lenses associated with the light detector and/or light emitter may be similarly formed from a diffuse material.

In still further embodiments, the reflective coating may be configured to be reflective to a particular frequency band of light. In one example, a reflective coating may be reflective to green light only. In such an example, the light emitter may be configured to emit green light and the light detector may be configured to collect green light. In other examples, different frequency bands may be used. In still further examples, more than one frequency may be used. More particularly, the reflective coating can be reflective to one or more bands of light, and can absorb all or substantially all other bands. In these examples, the frequency band of lights that the reflective coating reflects can be the band of light that the light emitter is configured to emit and that the light detector is configured to collect.

In still further embodiments, an additional coating may not necessarily be required. For example, one or more areas of an aluminum housing of a wearable electronic device can be polished to a mirror finish. In these examples, either the entire housing of the wearable electronic device can be polished to a mirror finish (or, alternative to a mirror finish, polished to a high degree to increase optical reflectivity), or distinct portions of the housing may be polished to increase optical reflectivity.

In still further embodiments, one or more of the reflective coatings and/or reflective coating and/or reflective surface finishes may be used in conjunction to increase the quantity of light received by the light detector of an optical sensing system.

Although many embodiments described herein refer to an optical sensing system with a single light emitter and a single light detector, such a configuration is not required. For example, in certain embodiments more than one light detector can be configured to collect light initially emitted from a single light emitter. In addition, more than one light emitter may be configured to emit light to be collected by a single light detector. In certain embodiments light emitters and light detectors can be included in pairs that are configured to emit and collect light at different frequencies. For example, a first light emitter and light detector pair may be configured to emit and collect light in a first frequency band and a second light emitter and light detector pair can be configured to emit and collect light in a second frequency band. In such embodiments, the first light emitter can be disposed adjacent to the same aperture as the second light emitter and, correspondingly, the first light detector can be disposed adjacent to the same aperture as the second light detector. In alternative embodiments, the first light emitter can be positioned in the same aperture as the second light detector, and the second light emitter can be positioned in the same aperture as the first light detector.

Further, although many embodiments described herein refer to an optical sensing system with a dedicated light emitter and a light detector, such a configuration is not required. For example, in some embodiments, the light emitter and/or light detector may also be associated with other features, functions, or operations of a wearable electronic device or optical sensing system. For example, a fitness or health tracking system can include a status-indicating light emitting diode to convey to a user an operational state of the fitness or health tracking system. In such an embodiment, the status-indicating light can be used as the light emitter of an optical sensing system. In this manner, both the light emitter and the light detector of an optical sensing system can be operated in one or more modes. For example, in one case, a light detector can be operated as a light emitter (e.g., light emitting diode and phototransistor). Similarly, a light emitter or light emitter can be operated as a light detector (e.g., phototransistor and light emitting diode).

Figure 7:
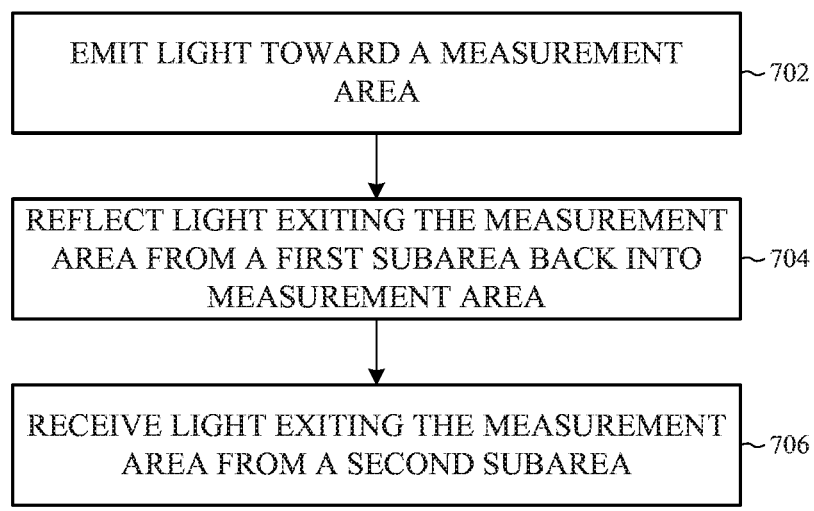
FIG. 7 depicts example operations of a method of operating an optical sensing system in accordance with embodiments described herein.

FIG. 7 depicts example steps of a method of operating an optical sensing system. The method can begin at operation 700 in which light can be emitted toward a measurement area. At 702, light exiting the measurement area from a first sub-area of the measurement area can be reflected back into the measurement area. At 704, light exiting the measurement area from a second sub-area of the measurement area can be received.

Many embodiments of the foregoing disclosure may include or may be described in relation to various methods of operation, use, manufacture, and so on. Notably, the operations of methods presented herein are meant only to be exemplary and, accordingly, are not necessarily exhaustive. For example, an alternate operation order, or fewer or additional steps, may be required or desired for particular embodiments.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not meant to be exhaustive or to limit the embodiments to the precise forms disclosed. It will be apparent to one of ordinary skill in the art that many modifications and variations are possible in view of the above teachings. In particular, any features described with respect to one embodiment may also be used in other embodiments, where compatible. Likewise, the features of the different embodiments may be exchanged, substituted, or omitted where compatible and appropriate.

The present disclosure recognizes that personal information data, including biometric and/or physiological data, in the present technology, can be of benefit to users. For example, the use of physiological or medical data can inform a user of the user's general health. In other examples, user medical data can be anonymously collected for providing to authorized medical professionals information about the health or fitness levels of a geographic or demographic group of patients. Further, other uses for personal medical or health information data that benefit the user, including biometric authentication data, are also contemplated by the present disclosure.

In addition, the present disclosure contemplates that the entities responsible for the collection, analysis, disclosure, transfer, storage, or other use of such personal information or data will comply with well-established privacy policies, privacy practices, and/or individual privacy preferences of particular users or authorized third parties. In particular, such entities should implement and consistently use privacy policies and practices that are generally recognized as meeting or exceeding industry or governmental requirements for maintaining personal information data private and secure, including the use of data encryption and security methods that meets or exceeds industry or government standards. For example, personal information from users should be collected for legitimate and reasonable uses of the entity and not shared or sold outside of those legitimate uses. Further, such collection should occur only after receiving the explicit and informed consent of the users or a user's legal guardian or representative. Additionally, such entities would take any needed steps for safeguarding and securing access to such personal information or data and ensuring that others with access to the personal information or data adhere to their privacy policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data, including biometric and medical data. That is, the present disclosure contemplates that hardware and/or software elements can be provided to prevent or block access to such personal information data. For example, users can select to remove, disable, or restrict access to certain health-related applications collecting users' personal health or fitness data.

What is claimed is:

1. An electronic device comprising:
   a housing with a surface;
   a reflective layer that is formed on the surface, wherein the reflective layer has first and second openings;
   a light emitter that emits light through the first opening; and
   a light detector that receives the light emitted by the light emitter through the second opening.

2. The electronic device defined in claim 1, wherein the light emitted by the light emitter is infrared light.

3. The electronic device defined in claim 1, wherein the light detector receives the light emitted by the light emitter through the second opening after the light reflects from an object.

4. The electronic device defined in claim 1, wherein the reflective layer is formed over the entire surface of the housing.

5. The electronic device defined in claim 1, further comprising a lens in the first opening.

6. The electronic device defined in claim 5, further comprising a selectively transparent layer in the second opening.

7. The electronic device defined in claim 6, wherein the lens diffuses the light from the light emitter.

8. The electronic device defined in claim 6, wherein the lens focuses the light from the light emitter.

9. The electronic device defined in claim 6, wherein the selectively transparent layer is transparent in a first frequency band of light and opaque in a second frequency band of light.

10. The electronic device defined in claim 1, wherein the light emitter is a light-emitting diode.

11. The electronic device defined in claim 1, further comprising:
    a processor disposed within the housing and coupled to the light emitter and the light detector;
    a display in communication with the processor;
    a button in communication with the processor;
    a rotary input device in communication with the processor; and
    a battery disposed within the housing.

12. The electronic device defined in claim 11, wherein the electronic device is configured to be worn on a wrist of a user.

13. An electronic device comprising:
    a housing with first and second opposing sides;
    a display on the first side of the housing;
    a lens on the second side of the housing;
    a light-emitting diode that emits infrared light through the lens;
    a filter on the second side of the housing;
    a light detector configured to detect the infrared light emitted by the light-emitting diode that passes through the filter.

14. The electronic device defined in claim 13, wherein the light detector is configured to detect the infrared light emitted by the light-emitting diode after the infrared light reflects from an object.

15. The electronic device defined in claim 13, further comprising:
    a processor configured to determine physiological data based on an amount of infrared light detected by the light detector.

16. The electronic device defined in claim 13, further comprising:
    a reflective layer on the second side of the housing with a portion interposed between the light-emitting diode and the light detector.

17. The electronic device defined in claim 13, wherein the filter is transparent in a first frequency band of light and opaque in a second frequency band of light.

18. The electronic device defined in claim 13, wherein the electronic device further comprises:
    a processor disposed within the housing and coupled to the light-emitting diode and the light detector;
    a button in communication with the processor;
    a rotary input device in communication with the processor; and
    a battery disposed within the housing.

19. The electronic device defined in claim 18, wherein the electronic device is configured to be worn on a wrist of a user.

20. An electronic device comprising:
    a housing with first and second cavities;
    a light emitter in the first cavity that emits light;
    a light detector in the second cavity that detects the light emitted by the light emitter after the light reflects from an object; and
    a reflector that is interposed between the first cavity and the second cavity.

* * * * *